United States Patent [19]
Penner et al.

[11] Patent Number: 5,859,348
[45] Date of Patent: Jan. 12, 1999

[54] IMIDAZOLINONE AND SULFONYL UREA HERBICIDE RESISTANT SUGAR BEET PLANTS

[75] Inventors: Donald Penner, Williamston; Terry R. Wright, Lansing, both of Mich.

[73] Assignee: Board of Trustees Operating Michigan State University, East Lansing, Mich.

[21] Appl. No.: 761,197

[22] Filed: Dec. 6, 1996

Related U.S. Application Data

[63] Continuation-in-part of Ser. No. 683,533, Jul. 17, 1996.
[51] Int. Cl.$^6$ ............... A01H 4/00; A01H 5/00; A01H 1/04; C12N 5/00
[52] U.S. Cl. ............... 800/230; 800/200; 435/410; 435/418; 47/58
[58] Field of Search ............... 435/240.4, 240.45, 435/240.46, 240.47, 240.48, 240.49, 240.5, 240.54, 410, 418; 800/200, 230; 47/58

[56] References Cited

U.S. PATENT DOCUMENTS

| | | | |
|---|---|---|---|
| 5,013,659 | 5/1991 | Bedbrook et al. | 435/172.3 |
| 5,141,870 | 8/1992 | Bedbrook et al. | 435/320.1 |
| 5,378,824 | 1/1995 | Bedbrook et al. | 536/23.6 |

FOREIGN PATENT DOCUMENTS 375875  4/1990  European Pat. Off. .

OTHER PUBLICATIONS

Renner, K. A. and G. E. Powell, Weed Technology 5:622–627 (1991).
Hart, et al. in Weed Science 40:378–383 (1992).
Hart, et al. in Weed Science 41:317–324 (1993).
Saunders et al. in Crop Science 32:1357–1360 (1992).
Newhouse et al., Theoretical and Applied Genetics 83:65–70 (1991).
Ray, Plant Physiol. 75:827–831 (1984).
Shaner, et al, Plant Physiol. 76:545–546 (1984).
Westerfield, J. Biol. Chem. 16:495–502 (1945).
Bradford, Anal. Biochem. 72:248–254 (1976).
Bernasconi et al., J. Biol. Chem. 270:17381–17385 (1995).
Current Protocols in Molecular Biology, J. Wiley and Sons, New York (1991).
Haughn et al., Molecular and General Genetics 211:266–271 (1988).
Lee et al., EMBO J. 7:1241–1248 (1988).

*Primary Examiner*—Douglas W. Robinson
*Assistant Examiner*—Thomas Haas
*Attorney, Agent, or Firm*—Ian C. McLeod

[57] ABSTRACT

Sugar beet plants which are resistant to both imidazolinone and sulfonylurea herbicides are described. The sugar beet plants are derived from susceptible cells by sequential selection of SU-R cells, plant regeneration, and re-selection for IM-R. The resistant sugar beet plants derived from the cells can be grown in fields where imidazolinones and sulfonylureas have been used for weed control.

14 Claims, 10 Drawing Sheets

FIG. 5B  Sir-13

0  0.3  1.1  4.4  17.5  70  280

FIG. 5C  Sur

FIG. 5D  93R30B 0  0.3  1.1  4.4  17.5  70  280

IMAZETHAPYR
(g ai ha⁻¹ + 1% 30-0-0 + 1% SunIt-II)
APPLIED at 298 L ha⁻¹

FIG. 6A wt / FIG. 6B Sir-13 / FIG. 6C Sur / FIG. 6D 93R30B

AC 299,263
(g ai ha⁻¹ + 1% 30-0-0 + 1% SunIt-II)
APPLIED at 239 L ha⁻¹

FIG. 7

| | $I_{50}$ (nM) | R/S |
|---|---|---|
| wt | 100 | --- |
| Sur | 5000 | 50X |
| Sir-13 | 270 | 3X |
| 93R30B | 20000 | 200X |

0  1  10  100  1k  10k  100k
[Flumetsulam] (nM)

FIG. 8

FIG. 9A wt
 FIG. 9B sir-13
 FIG. 9C Sur
 FIG. 9D 93R30B

CHLORSULFURON
(g ai ha$^{-1}$ + 0.25% NIS)
APPLIED at 239 L ha$^{-1}$

FIG. 10

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 5
        ( B ) TYPE: Amino acid
        ( C ) STRANDEDNESS: Single
        ( D ) TOPOLOGY: Linear     ( i i ) MOLECULE TYPE:
        ( A ) DESCRIPTION: peptide     ( i i i ) HYPOTHETICAL: No     ( i v ) ANTI-SENSE: No     ( v i ) ORIGINAL SOURCE:
        ( A ) ORGANISM: sugarbeet
        ( B ) STRAIN: wt
        ( C ) INDIVIDUAL ISOLATE:
        ( G ) CELL TYPE: N/A     ( i x ) FEATURE:
        ( A ) NAME/KEY:
        ( B ) LOCATION:
        ( C ) IDENTIFICATION METHOD: Sequencing
        ( D ) OTHER INFORMATION:

( x i ) SEQUENCE DESCRIPTION: SEQ ID NO:1:

Ala Pro Ala Trp Ser
                  5

( 2 ) INFORMATION FOR SEQ ID NO:2:

( i ) SEQUENCE CHARACTERISTICS:
        ( A ) LENGTH: 5
        ( B ) TYPE: amino acid
        ( C ) STRANDEDNESS: Single
        ( D ) TOPOLOGY: Linear     ( i i ) MOLECULE TYPE:
        ( A ) DESCRIPTION: peptide     ( i i i ) HYPOTHETICAL: No     ( i v ) ANTI-SENSE: No     ( v i ) ORIGINAL SOURCE:
        ( A ) ORGANISM: sugarbeet
        ( B ) STRAIN: Sir-13
        ( C ) INDIVIDUAL ISOLATE: N/A
        ( G ) CELL TYPE: N/A     ( i x ) FEATURE:
        ( A ) NAME/KEY:
        ( B ) LOCATION:
        ( C ) IDENTIFICATION METHOD: Sequencing
        ( D ) OTHER INFORMATION:

( x i ) SEQUENCE DESCRIPTION: SEQ ID NO:2:

Thr Pro Ala Trp Ser
                  5

( 2 ) INFORMATION FOR SEQ ID NO:3:

( i ) SEQUENCE CHARACTERISTICS:
        ( A ) LENGTH: 5
        ( B ) TYPE: amino acids
        ( C ) STRANDEDNESS: Single

```
        ( D ) TOPOLOGY: Linear ( i i ) MOLECULE TYPE:
            ( A ) DESCRIPTION: peptide ( i i i ) HYPOTHETICAL: No ( i v ) ANTI-SENSE: No ( v i ) ORIGINAL SOURCE:
            ( A ) ORGANISM: sugarbeet
            ( B ) STRAIN: Sur
            ( C ) INDIVIDUAL ISOLATE: N/A
            ( G ) CELL TYPE: N/A ( i x ) FEATURE:
            ( A ) NAME/KEY:
            ( B ) LOCATION:
            ( C ) IDENTIFICATION METHOD: Sequencing
            ( D ) OTHER INFORMATION:

( x i ) SEQUENCE DESCRIPTION: SEQ ID NO:3:

Ala  Ser  Ala  Trp  Ser
                        5

( 2 ) INFORMATION FOR SEQ ID NO:4:

( i ) SEQUENCE CHARACTERISTICS:
            ( A ) LENGTH: 5
            ( B ) TYPE: amino acids
            ( C ) STRANDEDNESS: Single
            ( D ) TOPOLOGY: Linear ( i i ) MOLECULE TYPE:
            ( A ) DESCRIPTION: peptide ( i i i ) HYPOTHETICAL: No ( i v ) ANTI-SENSE: No ( v i ) ORIGINAL SOURCE:
            ( A ) ORGANISM: sugarbeet
            ( B ) STRAIN: 9R30B
            ( C ) INDIVIDUAL ISOLATE: N/A
            ( G ) CELL TYPE: N/A ( i x ) FEATURE:
            ( A ) NAME/KEY:
            ( B ) LOCATION:
            ( C ) IDENTIFICATION METHOD: Sequencing
            ( D ) OTHER INFORMATION:

( x i ) SEQUENCE DESCRIPTION: SEQ ID NO:4:

Thr  Ser  Ala  Trp  Ser
                        5
```

IMIDAZOLINONE AND SULFONYL UREA HERBICIDE RESISTANT SUGAR BEET PLANTS

CROSS-REFERENCE TO RELATED APPLICATION

This application is a continuation-in-part of application Ser. No. 08/683,533, filed Jul. 17, 1996.

BACKGROUND OF THE INVENTION (1) Summary of the Invention

The present invention relates to a method for producing sugar beet plants (*Beta vulgaris* L.) which are resistant to both imidazolinone and sulfonylurea herbicides used for weed control. In particular, the present invention relates to sugar beet plants derived from a susceptible sugar beet by mutation of a gene encoding acetolactate synthase (ALS) also known as acetohydroxyacid synthase (AHAS) using the herbicides sequentially with cells in a culture medium.

(2) Description of Related Art

The prior art has described the genetic alteration of the acetolactate synthase gene by recombinant means as shown by U.S. Pat. Nos. 5,013,659; 5,141,870 and 5,378,824. This type of modification in sugar beet plants is shown by Example IV of the '824 patent. The results were less than satisfactory in producing plants which breed true for the herbicide resistance.

Saunders et al. in Crop Science 32:1357–1360 (1992) also describe the production of the sugar beet plant (CR1-B) which is resistant to sulfonylureas from the susceptible self-fertile clone (REL-1) by selection for mutant cells in a culture medium containing the herbicide. Various resistant plants were produced and cross-bred. Hart et al. (Weed Science 40378–383 (1992) and 41:317–324 (1993)) further characterized the resistant line and determined the resistance was due to altered ALS activity and showed no cross resistance to other ALS-inhibiting herbicides, and was coded for by a single, semidominant gene.

There are no publications describing imidazolinone resistance obtained by modifying ALS in sugar beet plants. There is no description in the literature of plants which are resistant to both imidazolinone and sulfonylurea herbicides. Various corn lines with imidazolinone resistance have been developed as described by Newhouse et al. Theoretical and Applied Genetics 83:65–70 (1991).

A commercial route to crop protection is the use of clinical "safeners" such as described in European Patent No. 375,875. This method introduces another chemical into the soil. The preferred method is to develop sugar beet plants which are resistant to the imidazolinone and sulfonylurea herbicides.

OBJECTS

It is therefore an object of the present invention to provide a method for imparting resistance to both imidazolinone and sulfonylurea herbicides in sugar beet plants by mutation of a acetolactate synthase gene encoding for this resistance. Further, it is an object of the present invention to provide sugar beet plants which are resistant to these herbicides. These and other objects will become increasingly apparent by reference to the following description and the drawings.

DESCRIPTION OF PREFERRED EMBODIMENTS

The present invention relates to a sugar beet plant material consisting of mutated cells with a mutated acetolactate synthase gene encoding the synthase, wherein the mutated cells have a resistance to both imidazolinone and sulfonylurea herbicides and wherein the resistance is transmitted by conventional cross-breeding of plants produced from the cells.

Further, the present invention relates to a method of producing a herbicide resistance in a sugar beet plant which comprises: exposing first cells of the sugar beet to an imidazolinone herbicide in a culture medium, wherein the first cells have a homozygous resistance to a sulfonylurea herbicide; and selecting for second cells having a resistance to both herbicides, wherein the resistance can be transmitted by cross-breeding of a plant containing the second cells.

Finally, the present invention relates to a method for imparting a herbicide resistance in a sugar beet which comprises: exposing first cells of sugar beet plant to an imidazolinone herbicide in a culture medium, wherein the first cells have a homozygous resistance to a sulfonylurea herbicide in a culture medium; selecting for second cells having a resistance to both herbicides; growing a first plant from the second cells, wherein the plant has the resistance to the herbicides; and cross-breeding the first plant with a second plant to produce a crossed plant which has the resistance to the herbicides.

Figure 1:
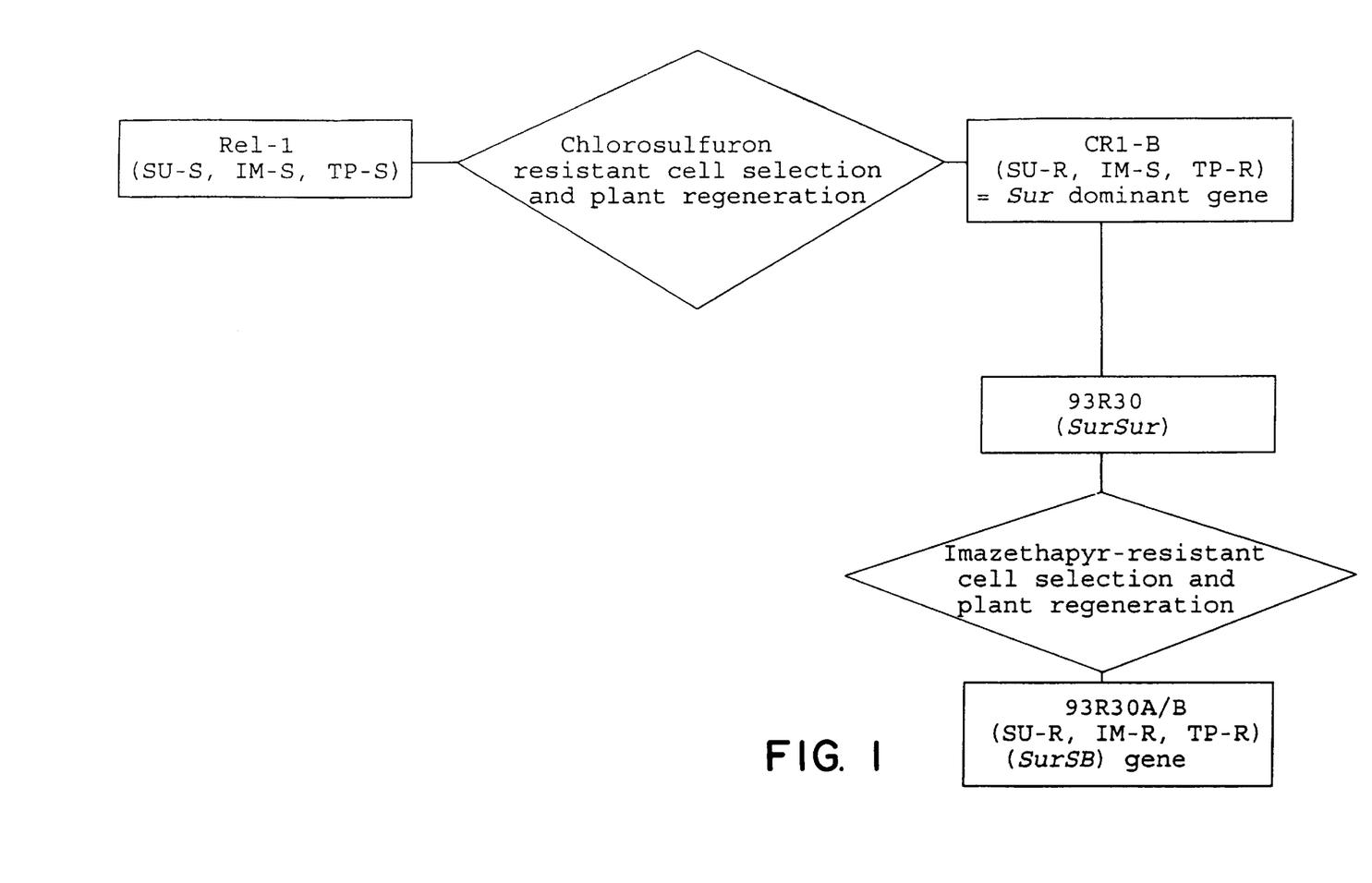
FIG. 1 is a schematic view of the method of the present invention for producing imidazolinone and sulfonylurea resistant sugar beet plants 93R30A or B. R=Resistant; IM=imidazolinone; S=sensitive; SU=sulfonylurea; Sur= ALS allele dominant for SU-R, TP-R and IM-S; SB=ALS allele dominant for SU-R, TP-R, and IM-R; TP=triazolopyrimidine. 93R30B is SU-R and IM-R and TP-R. 93R30 (not 93R30B) is homozygous for Sur allele (SU-R, IM-S). This was the starting material to obtain the imadazolinone resistance.

The sugar beet plant REL-1 (Regenerating, East Lansing-1) is available from Dr. Joseph Saunders, Research Geneticist, U.S. Department of Agriculture, East Lansing, Mich. and was released in 1987. It is available without cost. REL-1 is sensitive (S) to imidazolinone (IM-S), sulfonylurea (SU-S), and triazolopyrimidine sulfonanilide (TP-S) herbicides as indicated in FIG. 1. CR1-B was deposited with the American Type Culture Collection, Rockville, Md. on Mar. 21, 1997 as ATCC 97961. CR1-B is resistant to sulfonyl urea herbicides but not imidazolinone herbicides.

Using callus and suspension cultures a line which was heterozygous for imidazolinone and sulfonylurea resistance (IM-R and SU-R) was developed. This cell line (seed) has been deposited with the American Type Culture Collection as ATCC 97535 on May 6, 1996 under the Budapest Treaty and is referred to herein as 93R30B. The cell line is available upon request by name and number. By breeding with elite sugar beet plant lines, in particular *Beta vulgaris* L., especially commercially useful resistant sugar beet plants can be produced.

Sugar beet plants resistant to the imidazolinone herbicides, specifically imazethapyr, and sulfonylurea herbicides (chlorsulfuron) solve the soil residue problem from the use of that herbicide in sugar beet growing areas. Currently, there is a 40-month waiting period between the use of that herbicides and the future use of that field for growing sugar beet plants. Secondly, a high level of imidazolinone and sulfonylurea resistance allows use of the imidazolinone herbicides for weed control in sugar beets.

The following Examples show isolation and breeding of a novel sugar beet plant 93R30B as illustrated in FIG. 1.

EXAMPLE 1

1. Selection of imidazolinone and sulfonylurea resistant sugar beet variant 93R30B.

Description of Materials

Rel-1 (Regenerating East Lansing-1) is a highly regenerable male fertile sugar beet line used for initial cell selection for herbicide-resistant mutant to the sulfonylureas and is used as a sensitive control for most experiments.

CR1-B This sugar beet isolate was developed by plating Rel-1 cells on chlorsulfuron-containing media. This variant is sulfonylurea resistant with modest resistance to the triazolopyrimidine herbicide, flumetsulam, but no imidazolinone resistance. This variant has been described by Saunders et al. (Crop Sci. 32:1357–1360) and Hart et al. (Weed Sci. 40:378–383 and 41:317–324). The SU resistance gene has been labeled Sur.

93R30B This isolate was developed by plating cells of a highly regenerable, Sur homozygous sugar beet plant (descendant of CR1-B) on media containing imazethapyr.

EL-49 East Lansing 49, released by the USDA in 1993.

Sugar beet line homozygous for the Sur gene, used for a sulfonylurea-resistant, imazethapyr-sensitive control.

a. Plants were selected as source materials for somaclonal selection based on their ability to generate callus under high cytokinin conditions (in B1 media) and regenerate shoots from callus.

Protocol for B1 media:
30 g $L^{-1}$ sucrose
100 mg $L^{-1}$ myo-inositol
1.65 g $L^{-1}$ $NH_4NO_3$
1.90 g $L^{-1}$ $KNO_3$
0.44 g $L^{-1}$ $CaCl_2.2H_2O$
0.37 g $L^{-1}$ $MgSO_4.7H_2O$
0.17 g $L^{-1}$ $KH_2PO_4$
6.2 mg $L^{-1}$ $H_3BO_3$
16.8 mg $L^{-1}$ $MnSO_4.H_2O$
10.6 mg $L^{-1}$ $ZnSO_4.7H_2O$
0.88 mg $L^{-1}$ KI
0.25 mg $L^{-1}$ $Na_2MoO_4.2H_2O$
0.025 mg $L^{-1}$ $CuSO_4.5H_2O$
0.025 mg $L^{-1}$ $CoCl_2.6H_2O$
37.3 mg $L^{-1}$ $Na_2EDTA$
27.8 mg $L^{-1}$ $FeSO_4.7H_2O$
1 mg $L^{-1}$ thiamine
0.5 mg $L^{-1}$ pyridoxine
0.5 mg $L^{-1}$ nicotinic acid
1 mg$L^{-1}$ benzylaminopurine
pH 5.95

B1 solid media was autoclaved with 9 g $L^{-1}$ plant culture agar and modified with filter-sterilized herbicide stock solutions as needed for selection scheme. Agar media was poured into 15×100 mm disposable plastic petri dishes.

B1 liquid media was added in 40 ml aliquots to 125 ml Erlenmeyer flasks and autoclaved for use in liquid suspension cultures.

For selection of the imidazolinone resistant variant, 93R30B, the source material was 93R30 (a Sur homozygotic descended from CR1-B).

In particular:

1. Cells from Rel-1 (SU-S, IM-S, TP-S) were placed into culture where cells were selected for their ability to grow on chlorsulfuron and a plant was regenerated, CR1-B (described by Saunders et al, Crop Sci, 32:1357–1360 (1992)).

2. CR1-B was crossed with 293 (a more typical beet), the F1 selfed and homozygous plants for SU-R, IM-S, TP-R were identified. A plant known as EL-49 meeting this description was released in 1993 by Saunders (the gene was called Sur and this was homozygous for it).

3. At a later date, descendants of CR1-B homozygous for Sur were selected for their ability to regenerate plants from culture. They then served as source material (e.g., 93R30) for imazethapyr selection in culture.

4. From the above selection, the isolates known as 93R30A and 93R30B were derived and plants regenerated. These had the characteristics of CR1-B plus IM-R. The gene responsible for IM-R appears to be an altered form of Sur and has been given the identity of SB.

Figure 2:
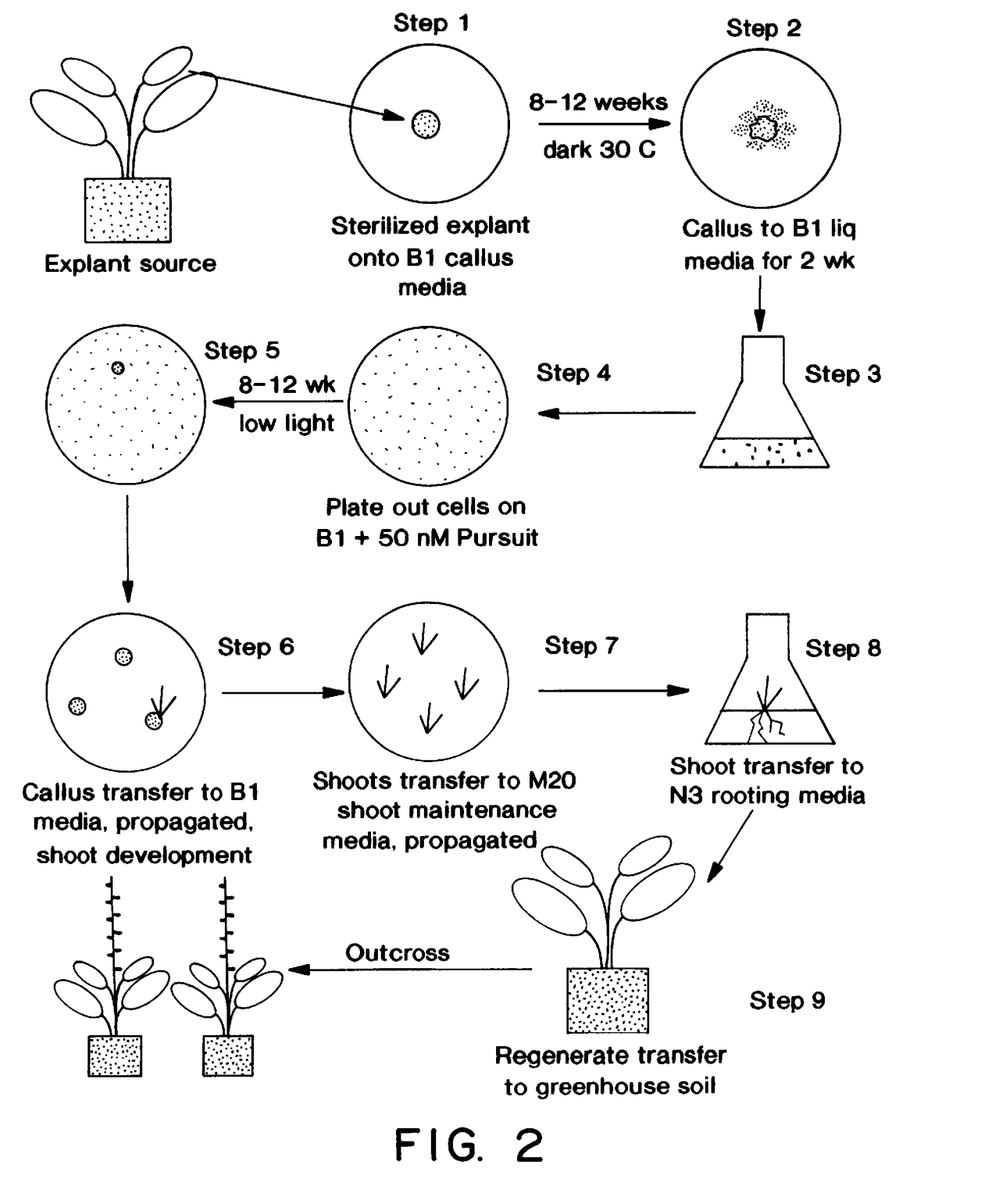
FIG. 2 is a flow diagram showing the detailed steps in producing a mutant sugar beet plant.

Leaf disk explants were prepared from rapidly expanding leaves of the source plant (93R30). The leaves were surface sterilized (step 1) by two successive 20-minute washes with 15% commercial bleach plus 0.025% Triton X-100 (T-9280, Sigma Chem. Co., St. Louis, Mo.). Leaves were rinsed twice with sterile deionized water. Leaf disks were cut using a flame-sterilized #3 cork borer.

Leaf disks were placed aseptically onto solid B1 media (step 2). Disks were incubated in the dark at 30° C. for 4–8 weeks until friable, white callus tissue had proliferated from the leaf disk. Callus tissue were separated mechanically with forceps and subsequently transferred to 125 ml Erlenmeyer flasks (step 3) containing 40 ml liquid B1 media. Flasks were placed onto a gyratory shaker at 50 Hz under low intensity fluorescent lighting (30 $\mu E/m^2$ s). Liquid cultures were subcultured with fresh El media after 1 week.

Two weeks after liquid culture initiation, cell clumps were separated using a cell dissociation sieve (Sigma CD-1) with a 60 mesh screen. Approximately two-thirds volume of the liquid media was removed following cell sedimentation. In step 4, cells were resuspended in remaining media and 1 ml aliquots were spread evenly over solid B1 media supplemented with 50 nM imazethapyr (PURSUIT, American Cyanamid, Wayne, N.J.) herbicide. Plates were wrapped and incubated in dim fluorescent light (5–10 $\mu E/m^2$ s) for 8–12 weeks.

c. At 50 nM imazethapyr concentration, all sensitive cells died. Cell clumps that survived and grew at this concentration are identified as possible resistant variants. In step 5, these cell clumps (1–3 mm in diameter) were transferred to fresh B1 solid media without herbicide and allowed to grow under low light (10–20 µE/m² s). Each putatively resistant variant was individually identified and maintained separately.

d. In step 6, white, friable callus was subdivided every 4–6 weeks to fresh El solid media until an individual shoot(s) grew from the callus. These shoots were transferred to shoot maintenance media (M20) as follows:

Protocol for M20 media:
30 g L$^{-1}$ sucrose
100 mg L$^{-1}$ myo-inositol
1.65 g L$^{-1}$ NH$_4$NO$_3$
1.90 g L$^{-1}$ KNO$_3$
0.44 g L$^{-1}$ CaCl$_2$.2H$_2$O
0.37 g L$^{-1}$ MgSO$_4$.7H$_2$O
0.17 g L$^{-1}$ KH$_2$PO$_4$
6.2 mg L$^{-1}$ H$_3$BO$_3$
16.8 mg L$^{-1}$ MnSO$_4$.H$_2$O
10.6 mg L$^{-1}$ ZnSO$_4$.7H$_2$O
0.88 mg L$^{-1}$ KI
0.25 mg L$^{-1}$ Na$_2$MoO$_4$.2 H$_2$O
0.025 mg L$^{-1}$ CuSO$_4$.5 H$_2$O
0.025 mg L$^{-1}$ CoCl$_2$.6H$_2$O
37.3 mg L$^{-1}$ Na$_2$EDTA
27.8 mg L$^{-1}$ FeSO$_4$.7 H$_2$O
1 mg L$^{-1}$ thiamine
0.5 mg L$^{-1}$ pyridoxine
0.5 mg L$^{-1}$ nicotinic acid
0.25 mg L$^{-1}$ benzylaminopurine
pH 5.95

M20 solid media was autoclaved with 9 g L$^{-1}$ plant culture agar and modified with filter-sterilized herbicide stock solutions as needed for selection scheme. Agar was poured into 20×100 mm disposable plastic petri dishes.

Shoot cultures were maintained under 10–20 µE/m² s fluorescent lighting and propagated by dissecting shoot cultures with a scalpel blade. Candidate shoot cultures were propagated and assessed for level of resistance as described hereinafter.

2. Level of imidazolinone, sulfonylurea and triazolopyrimidine sulfonanilide resistance in shoot culture.

In step 7, shoot cultures were assessed for herbicide resistance by placing three small, consistently sized shoot cuttings on each plate of M20 media supplemented with logarithmically increasing concentrations of imidazolinone herbicide, sulfonylurea or triazolopyrimidine sulfonanilide ranging from 1 nM to 0.1 mM. 93R30 culture responses were compared to that of shoot cultures of a sensitive control (Rel-1) and a chlorsulfuron resistant, imidazolinone sensitive control (EL-49). Shoot cultures were maintained at 20 µE/m² s light intensity at 25° C. for 3 weeks. Shoot culture response was determined by rating shoot injury and fresh weight 3 weeks after transfer to selective media. Magnitude of herbicide resistance was determined by the ratio of resistant to sensitive I$_{50}$ values (the herbicide concentration causing 50 percent injury).

The cross resistance characteristics of each variant were determined in the manner above by substituting the herbicide used in the media. In shoot culture 93R30B showed a 3600 fold level of resistance to imazethapyr, a 10,000 fold resistance to chlorsulfuron and showed a 60 fold cross resistance to the triazolopyrimidine sulfonanilide herbicide, flumetsulam as shown in Table 1. For comparison EL-49 showed only a 3 fold level of resistance to imazethapyr.

TABLE 1

Magnitude of shoot culture resistance and cross-resistance:

| Herbicide | Herbicide family[6] | Rel-1 I$_{50}$[5] (µM) | 93R30B I$_{50}$ (µM) | 93R30B R/S[4] | EL-49 I$_{50}$(µM) | EL-49 R/S |
|---|---|---|---|---|---|---|
| Imazethapyr | IM | 0.018 | 64 | 3600 X | 0.053 | 3 X |
| Imazamethabenzmethyl | IM | 0.80 | >100 | >125 X | 20 | 25 X |
| Imazaquin | IM | 0.040 | 16 | 400 X | 0.040 | 1 X |
| AC299,263[1] | IM | 0.030 | 40 | 1400 X | 0.070 | 3 X |
| Chlorsulfuron[2] | SU | 0.0025 | 25 | 10000 X | 25 | 10000 X |
| Flumetsulam[3] | TP | 0.028 | 1.7 | 60 X | 1.1 | 40 X |

[1]Imadazolinone RAPTOR (American Cyanamid, Wayne, NJ)
[2]Sulfonylurea - GLEAN (Dupont, Wilmington, DE)
[3]Triazolopyrimidine sulfonanilide (BROADSTRIKE, Dow Elanco, Indianapolis, IN)
[4]R/S = ratio of resistant to sensitive control I$_{50}$ values for the specific herbicide being tested.
[5]I$_{50}$ is the concentration of herbicide required to cause 50% injury to the shoot culture.
[6]Herbicide family classifications: IM, imidazolinone; SU, sulfonylurea; and TP, trizolopyrimidine sulfonanilide.

3. Plant regeneration and breeding.

In step 8, shoot cultures of 93R30B were regenerated to whole plants in a similar manner. Two weeks following previous shoot subculture, 93R30B shoots were transferred to 125 ml Erlenmeyer flasks containing 40 ml N3 rooting media.

Protocol for N3 media:
30 g L$^{-1}$ sucrose
100 mg L$^{-1}$ myo-inositol
1.65 g L$^{-1}$ NH$_4$NO$_3$
1.90 g L$^{-1}$ KNO$_3$
0.44 g L$^{-1}$ CaCl$_2$.2H$_2$O
0.37 g L$^{-1}$ MgSO$_4$.7H$_2$O
0.17 g L$^{-1}$ KH$_2$PO$_4$
6.2 mg L$^{-1}$ H$_3$BO$_3$
16.8 mg L$^{-1}$ MnSO$_4$.H$_2$O
10.6 mg L$^{-1}$ ZnSO$_4$.7H$_2$O
0.88 mg L$^{-1}$ KI
0.25 mg L$^{-1}$ Na$_2$MoO$_4$.2H$_2$O
0.025 mg L$^{-1}$ CuSO$_4$.5H$_2$O
0.025 mg L$^{-1}$ CoCl$_2$.6H$_2$O
37.3 mg L$^{-1}$ Na$_2$EDTA
27.8 mg L$^{-1}$ FeSO$_4$.7H$_2$O
1 mg L$^{-1}$ thiamine
0.5 mg L$^{-1}$ pyridoxine 0.5 mg L$^{-1}$ nicotinic acid
3 mg L$^{-1}$ naphthalene acetic acid
pH 5.95
N3 media added in 40 ml aliquots to 125 ml Erlenmeyer flasks, 9 g L$^{-1}$ agar (0.45 g) added to each flask, and autoclaved for use in rooting of shoot cultures. Cultures were then transferred to 24 hour per day light under medium light intensity (40–60 $\mu$E/m$^2$ s) at 25° C. Roots generally formed 6–8 weeks later.

In step 9, rooted shoots (R$_0$ generation) were then transferred to Baccto (Michigan Peat Co., Houston, Tex.) potting mix in the greenhouse. In step 10, R$_0$ plants of 93R30B regenerates were crossed with a smooth-root sugar beet called 293 or with REL-1. F$_1$ seed from these crosses were self-fertilized to yield F$_2$ seed. It was presumed that imidazolinone resistance was a dominant or semi-dominant monogenic trait. F$_2$ generation plants resulting from self fertilization of imidazolinone and sulfonylurea-resistant F$_1$ plants should be segregating in a 1 homozygous resistant: 2 heterozygous resistant: 1 homozygous sensitive ratio for both imidazolinone and sulfonylurea resistances.

Evidence suggests that imidazolinone resistance is a dominant trait in 93R30B. This conclusion is derived from evidence examining F$_1$ progeny of crosses between 93R30B and herbicide sensitive, male fertile sugar beet lines 293 or Rel-1 which segregate in a 1:1 fashion for IM-R or IM-S. Likewise, in all F$_2$ or Backcross (BC$_1$) plants tested to date, IM-R and SU-R co-segregate. This suggests these two resistances are linked and due to separate alterations to the same ALS allele. Resistance or sensitivity of F$_1$ plants to imazethapyr and chlorsulfuron has been determined using a non-destructive leaf disk expansion assay.

Assay Protocol:

This protocol is a non-destructive test designed to screen beets segregating for herbicide resistance early to determine their status as resistant or susceptible without having to spray the beets postemergence in the greenhouse.

1. Newly expanding leaf was excised from plant (at least the 4th true leaf).
2. The leaf was surface sterilized with two 20-minute washes with 15% commercial bleach+0.025% Triton X-100, then rinsed twice with sterile distilled water.
3. Leaf disk explants were cut with flame-sterilized #3 cork borer.
4. Leaf disks transferred to B1 media containing no herbicide, 100 nM imazethapyr or 100 nM chlorsulfuron. Plates were divided into four sections so four samples an be tested with a single plate. Four to five leaf disks were added to each plate for each sample.
5. Plates were wrapped and incubated at 25° C. for 4–7 days under low light (approximately 10 $\mu$E/m$^2$ s).
6. Resistant samples were identified by their ability to live and expand on the selective media. Sensitive samples will not expand and will turn yellow to brown. Effects were compared to the expansion of leaf disks placed on no-herbicide media to insure accurate determination of the expected level of disk expansion.

4. ALS target enzyme response to imazethapyr

Standard procedures were utilized to partially purify ALS from rapidly expanding leaves of greenhouse-grown sugar beet plants (Hart, et al. Weed Science 40:378–383 (1992)). Extracts from heterozygous 93R30B F$_1$ plants and Rel-1 S$_1$ seed were assayed for ALS activity in the presence of logarithmically increasing concentrations of imazethapyr. ALS activity was determined from leaf extracts of REL-1 and 93R30B sugarbeet lines. Plants were grown in the greenhouse as described above to the four to six leaf stage. ALS activity from fresh extracts was determined in the presence of imazethapyr and chlorsulfuron at logarithmically increasing concentrations. The methods and procedures used were modified from those outlined by Ray (Plant Physiol. 75:827–831 (1984)) and Shaner, et al. (Plant Physiol. 76:545–546 (1984)). Ten g of sugarbeet leaves were homogenized in 40 ml cold homogenization buffer (0.1M K$_2$HPO$_4$, pH 7.5, 1 mM sodium pyruvate, 0.5 mM MgCl$_2$, 0.5 mM thiamine pyrophosphate, 10 $\mu$M of flavin adenine dinucleotide, 10% by vol glycerol) plus 2.5 g polyvinylpolypyrrolidone. The homogenate was filtered through eight layers of cheesecloth and centrifuged at 27,000 g for 20 minutes. The supernatant was removed and brought to 50% saturation with (NH$_4$)$_2$SO$_4$. This solution was kept at 0° C. for 1 hour, then centrifuged at 18,000 g for 15 minutes, the pellet redissolved in 1 ml resuspension buffer (0.1M K$_2$HPO$_4$, pH 7.5, 20 mM sodium pyruvate, 0.5 mM MgCl$_2$) and desalted on a Sephadex G-25 PD-10$^5$ column. The enzyme extracts were assayed immediately.

ALS activity is measured by adding 0.2 ml of enzyme preparation (diluted 3:1 with resuspension buffer) to 1.3 ml of reaction buffer (25 mM K$_2$HPO$_4$, pH 7.0, 0.625 mM MgCl$_2$, 25 mM sodium pyruvate, 0.625 mM thiamine pyrophosphate, 1.25 $\mu$M flavin adenine dinucleotide) and incubated at 35° C. for 1 hour. Reaction mixtures contained a final concentration of 0, 4, 40, 400, 4000, 40000, 400000, or 4000000 nM imazethapyr or 0, 0.9, 9, 90, 900, 9000, 90000 nM chlorsulfuron. The reaction was stopped by adding 50 $\mu$l of 6N H$_2$SO$_4$ and incubating at 60° C. for 15 minutes. This procedure as described by Westerfield (J. Biol. Chem. 16:495–502 (1945)) also decarboxylates the ALS enzyme product, acetolactate, to form acetoin. A colored acetoin complex was formed by adding 1 ml 2.5% by weight $\alpha$-naphthol and 0.25% by weight creatine in 2.5N NaOH and incubating at 60° C. for 15 minutes.

Purchased acetoin was used as a standard for the colorimetric reaction. Acetoin concentrations were determined by measuring the absorption of the reaction solution at 530 nm. Experiments with each herbicide were repeated with three replications in each. Protein concentrations of the extracts was determined by the method of Bradford (Anal. Biochem. 72:248–254 (1976)) using bovine serum albumin for the standard curve.

Figure 3:
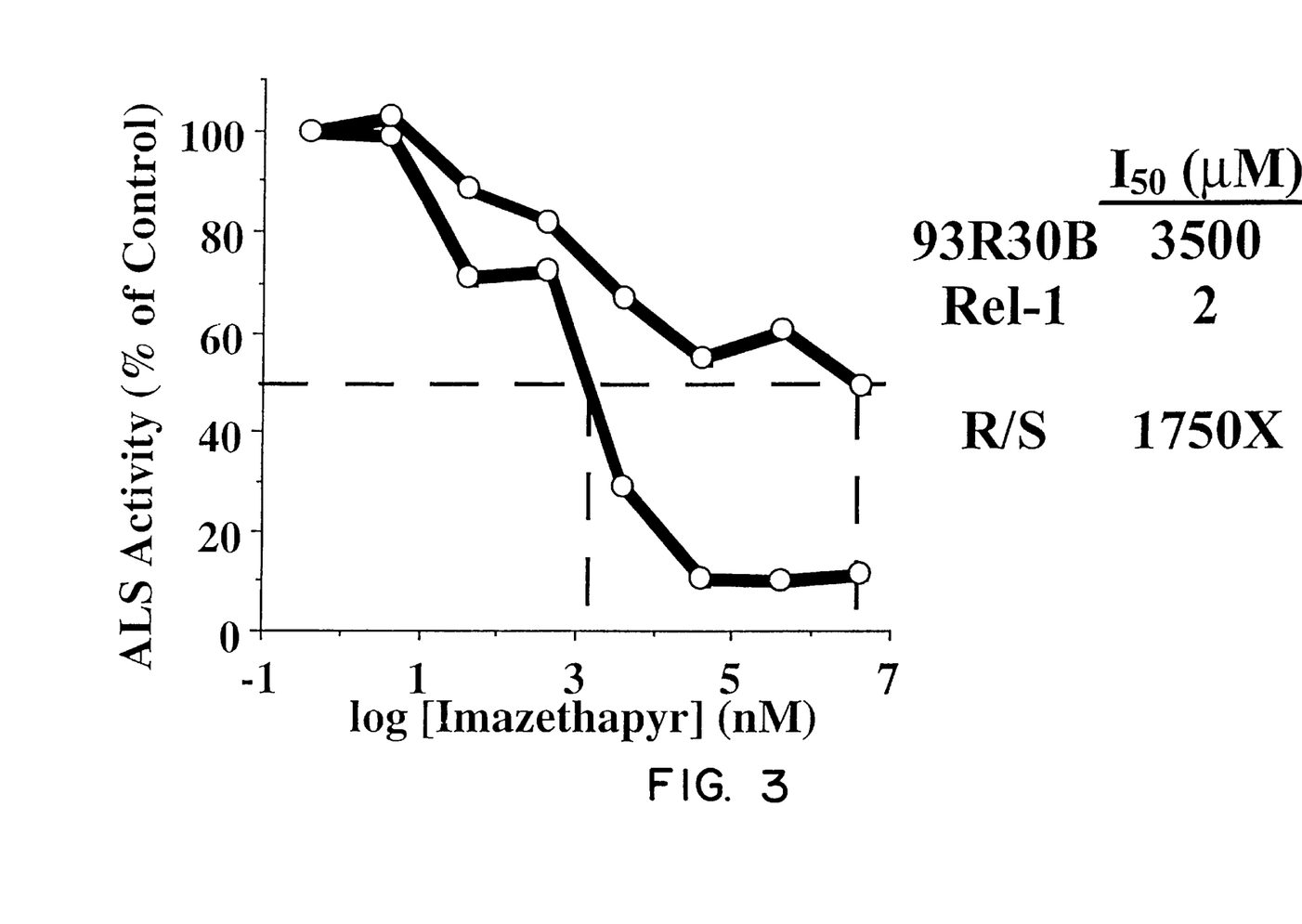
FIG. 3 is a graph showing an ALS assay for 93R30B resistance to imazethapyr.

Experiments were conducted twice and treatments replicated three times. FIG. 3 shows the response of ALS extracts from 93R30B and the sensitive Rel-1. 93R30B shows a 1750-fold level of resistance to imazethapyr at the enzyme level (as determined by the ratio of I$_{50}$'s for the resistant and sensitive lines)

5. ALS gene copy number

Southern blot analysis was conducted to determine the number of ALS gene copies present in sensitive sugar beet. Genomic DNA was isolated from sensitive F$_3$ plants descended from the original Sir-13 mutant and analyzed using commonly practiced techniques (Current Protocols in Molecular Biology, J. Wiley and Sons, New York (1991)). Likewise, genomic DNA from a commercial sugar beet variety was analyzed. In both sugar beet lines, a single copy of the ALS gene was detected. This data would indicate that all ALS enzyme activity of a homozygous mutant-type sugar beet would consist of the resistant enzyme form. This also supports the belief that the SB change observed in 93R30B isolate is an altered form of the Sur ALS allele. This was confirmed as described below.

6. ALS gene mutation

To determine the molecular basis for ALS enzyme resistance, standard techniques were used to sequence two regions of the ALS gene where all previously reported herbicide resistance mutations have occurred (Current Protocols in Molecular Biology, J. Wiley and Sons, New York (1991)). The sugar beet ALS gene had previously been sequenced (U.S. Pat. No. 5,378,824) and Polymerase Chain Reaction (PCR) primers designed to amplify the two regions of the gene responsible for previously reported cases of plant herbicide resistance. Comparison of sequence data from SU-R IM-S TP-R (Sur), SU-R IM-R TP-R (SB), and sensitive (Rel-1) sugar beets indicated 93R30B's herbicide resistance traits were due to two independent mutations in the ALS gene.

The mutation causing SU-R IM-S TP-R (Sur) is the result of a single nucleotide change from cytosine to thymine at position 562 in the nucleotide sequence which results in a serine for proline substitution at position 188 in the sugar beet ALS amino acid sequence. This site has previously been implicated in sulfonylurea resistance in *Arabidopsis thaliana* (Haughn et al., Molecular and General Genetics 211:266–271 (1988)), tobacco (Lee, et al., EMBO J. 7:1241–1248 (1988)), and in yeast (U.S. Pat. No. 5,378, 824). No other bases changes were observed from wild type nucleotide sequence in the two regions of the ALS gene examined.

The mutation causing SU-R IM-R TP-R (SB) is the result of two independent mutations in the ALS nucleotide sequence resulting in two different amino acid changes. The first change is identical to the Sur mutation described above. This observation was expected since a sugarbeet plant (93R30) served as the starting material for IM-R selection. In addition to this point mutation, an additional single nucleotide change from guanine to adenine at position 337 was observed. This second mutation results in a threonine for alanine substitution at position 113 in the sugar beet ALS amino acid sequence. This site has previously been implicated in imidazolinone resistance in cocklebur (Bernasconi et al., J. Biol. Chem. 270:17381–17385 (1995)) and for sulfonylurea resistance in yeast (U.S. Pat. No. 5,378,824). No other bases changes were observed from wild type nucleotide sequence in the two regions of the ALS gene examined.

The following information shows herbicide resistant synergism of possible $Ala_{113} \rightarrow Thr$ and $Pro_{188} \rightarrow Ser$ mutations.

Figure 4:
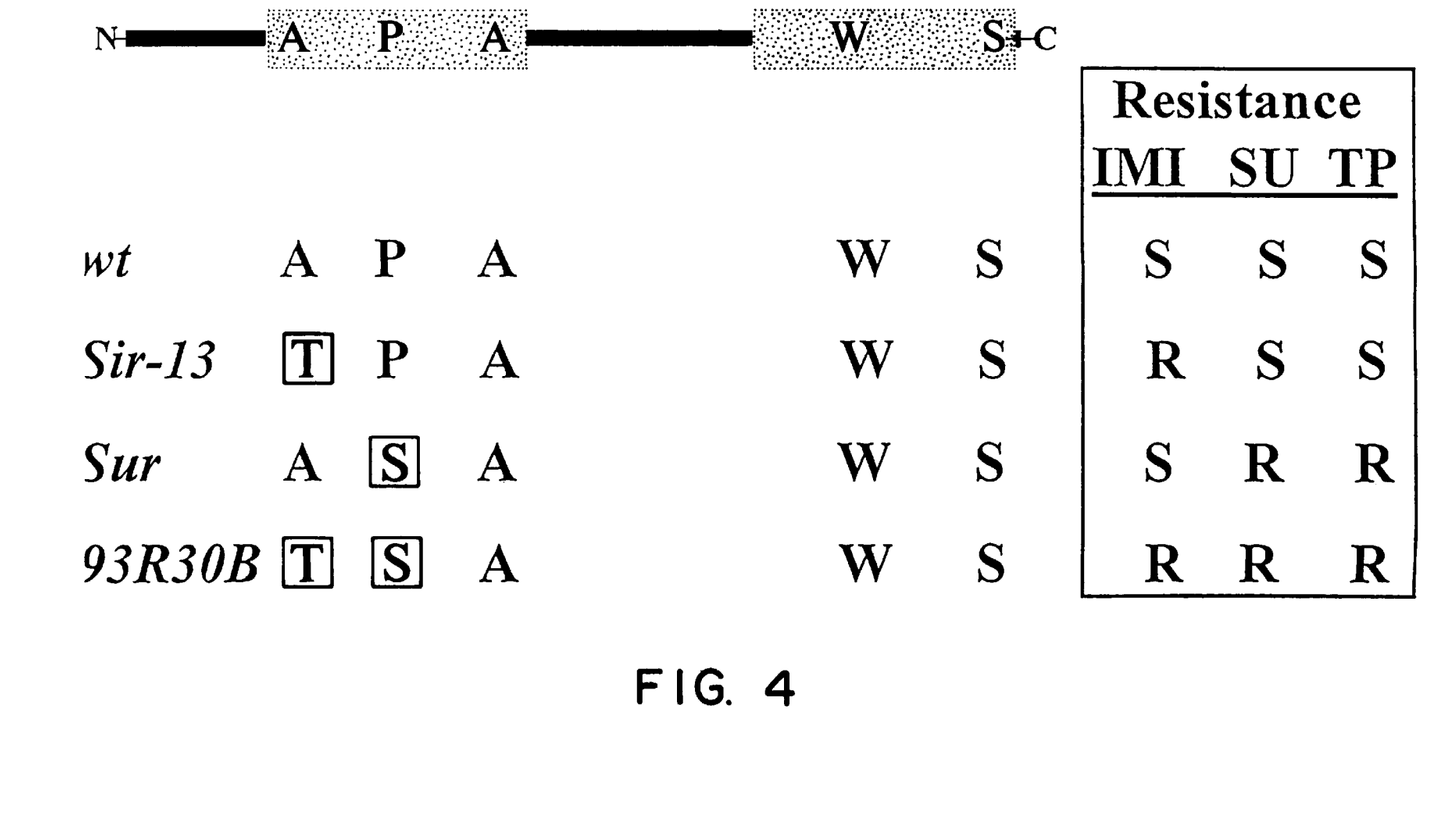
FIG. 4 is a chart showing amino acid substitutions observed for wildtype (wt) three mutant sugarbeets (Sir-13, Sur, and SB) and corresponding herbicide resistance. Only amino acid residues reported in the literature which account for herbicide resistance in plants are included. One letter amino acid codes are as follows: A=alanine, P=proline, W=tryptophan, S-serine, and T=threonine). Boxed letters indicated changes from the wildtype sequence.
Figure 5A:
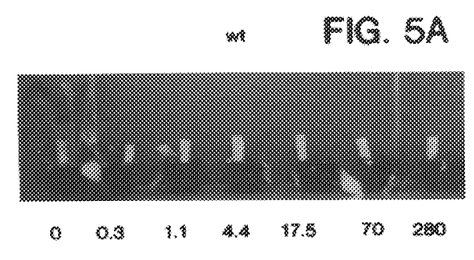
FIGS. 5A to 5D are photographs showing whole plant sugarbeet response to imazethapyr applied postemergence.
Figure 5B:
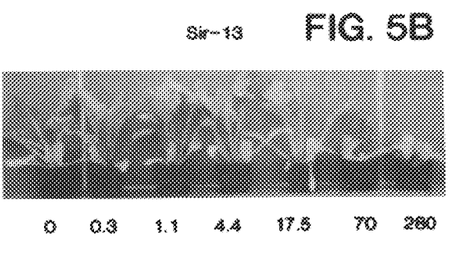
Figure 5C:
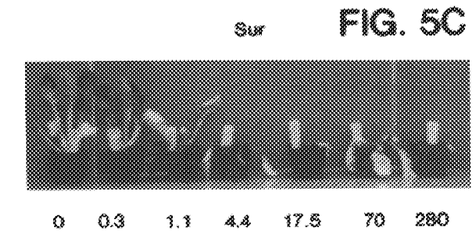
Figure 5D:
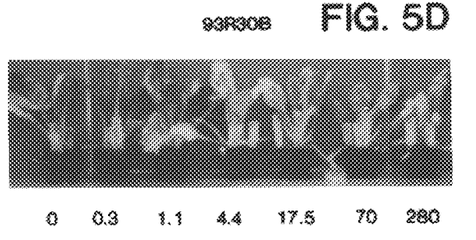
Figure 6A:
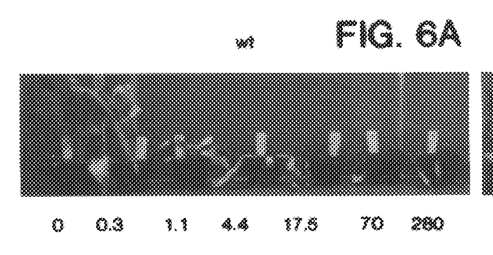
FIGS. 6A to 6D are photographs showing whole plant sugarbeet response to AC 299,263 applied postemergence.
Figure 6B:
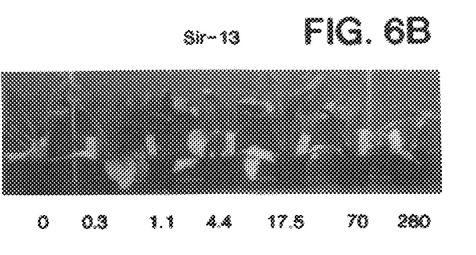
Figure 6C:
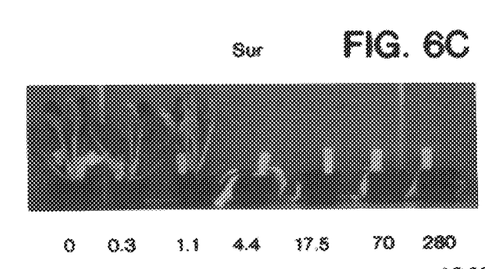
Figure 6D:
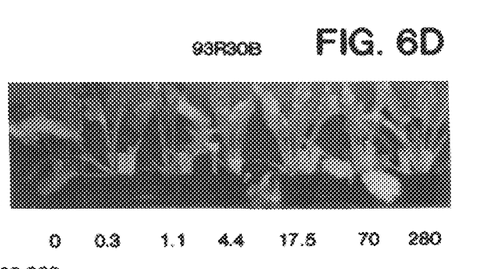

The SB sugarbeet ALS gene double mutation provides herbicide resistance to the combination of the chemical families afforded by each of the single mutant sugarbeets individually (i.e., Sur and Sir-13). FIG. 4 displays the basic family cross resistance characteristics of the two single mutants (Sur and Sir-13) and the double mutant (SB). The amino acids depicted in FIG. 4 represent the 5 strictly conserved residues reported in the literature to be involved in ALS-inhibiting herbicide resistance in plants. The interaction of the independent mutations within the double mutant enzyme (and corresponding plants) is unique. The combination of the IM-specific resistance seen with the Sir-13 amino acid substitution ($Ala_{113} \rightarrow Thr$) and the SU- and TP-resistance observed with the Sur substitution ($Pro_{188} \rightarrow Ser$) result in a sugarbeet 93R30B (a.k.a. SB) resistant to all three classes of herbicide chemistry.

Resistances, however, are not additive. Instead, the mutations are synergistic with respect to resistance to the imidazolinone herbicides imazethapyr and AC 299,263. This phenomenon can be seen visually in FIGS. 5 and 6 and quantitatively in Table 2.

TABLE 2

Whole Plant Sugarbeet Response to POST ALS-Inhibiting Herbicides

| | | Sugarbeet Line | | | |
|---|---|---|---|---|---|
| Herbicide | Class | Rel-1 $I_{50}$ (g ha$^{-1}$) | Sir-13 R/S | Sur R/S | 93R30B R/S |
| Imazethapyr | IMI | 0.5 | 100 X | 3 X | 300 X |
| AC299,263 | IMI | 1.1 | 130 X | 4 X | >250 X |
| Chlorsulfuron | SU | 0.07 | 1 X | >1000 X | 20 X |
| Sulfometuron | SU | 0.2 | 1 X | 23 X | 4 X |

Figure 7:
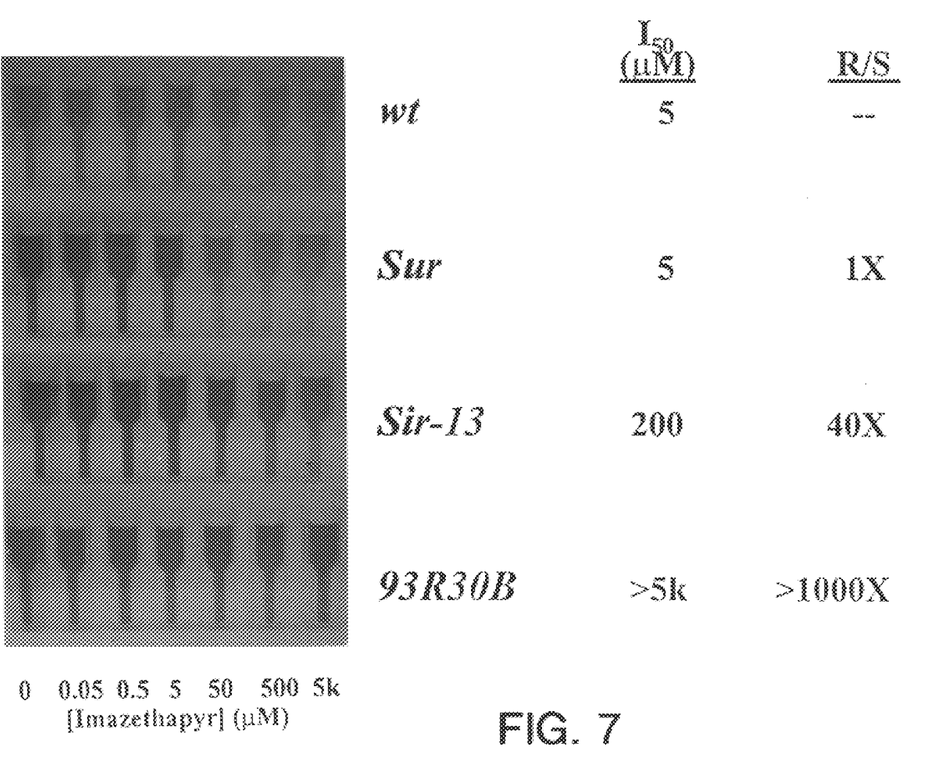
FIG. 7 is a photograph showing ALS enzyme response to imazethapyr in vitro.

The single mutation sugarbeets, Sur and Sir-13, exhibit 3 and 100 fold resistance to imazethapyr; whereas, the double mutant, SB, is 300 fold resistant to the herbicide when applied postemergence to whole plants. Support for this synergism is provided by observed response of the ALS enzyme from each of the mutants to imazethapyr (FIG. 7). Again, a synergistic resistance to the herbicide in the double mutant, SB (>1000X), versus the single mutants, Sur (1X) and Sir-13 (40X), alone.

Figure 8:
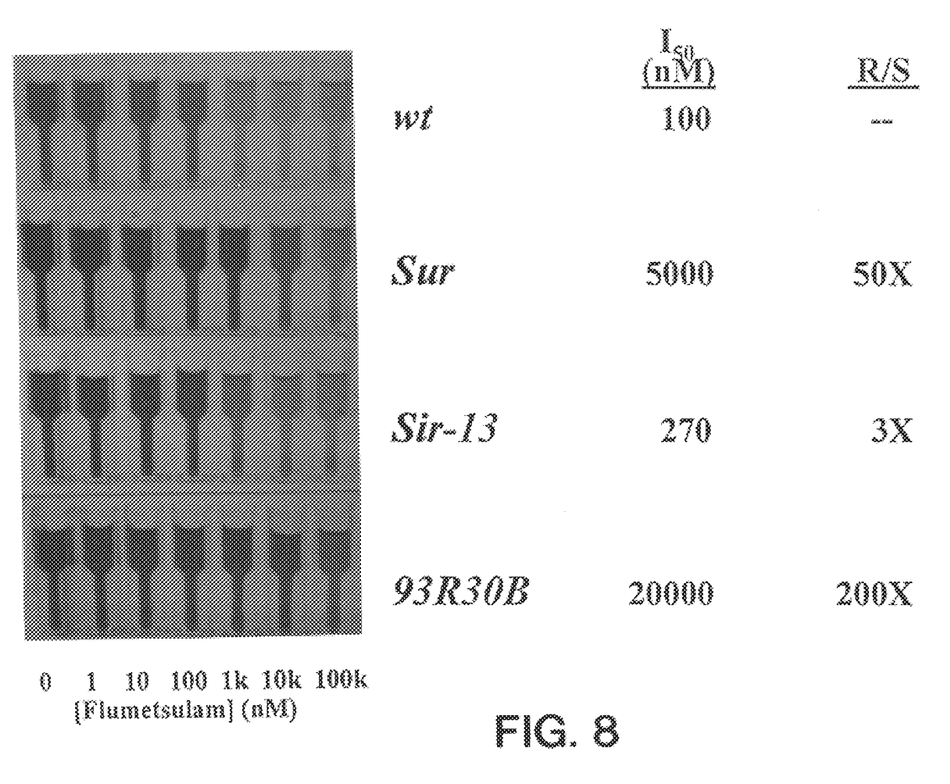
FIG. 8 is a photograph showing ALS enzyme response to fumetsulam in vitro.
Figure 9A:
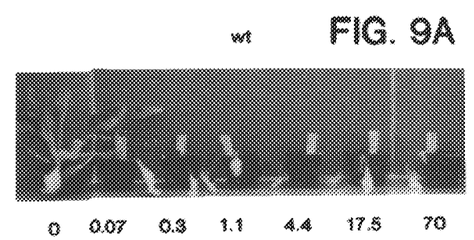
FIGS. 9A to 9D are photographs showing whole plant sugarbeet response to chlorosulfuron applied postemergence.
Figure 9B:
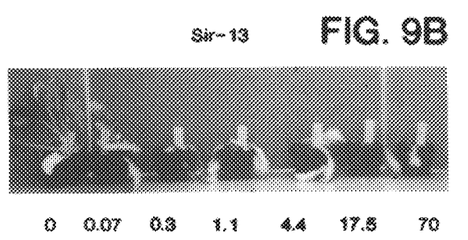
Figure 9C:
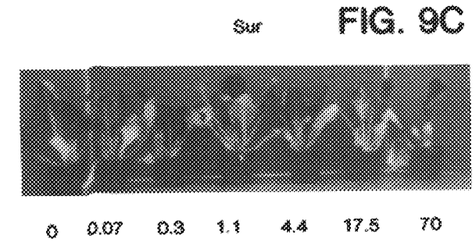
Figure 9D:
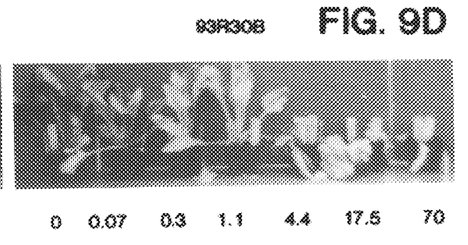
Figure 10:
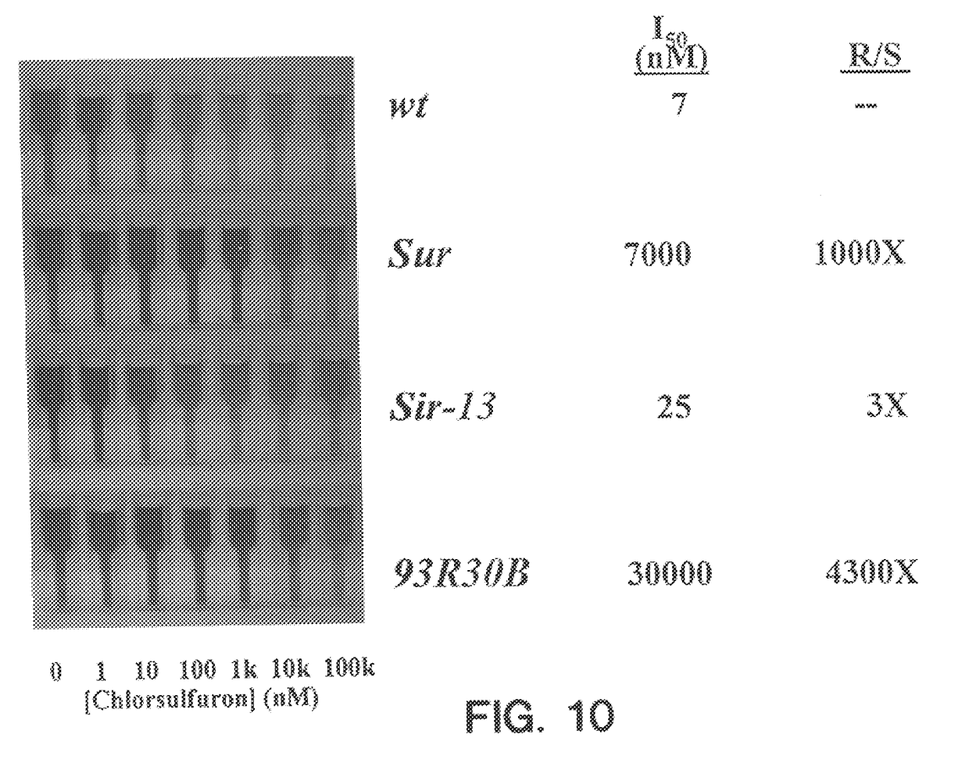
FIG. 10 is a photograph showing ALS enzyme response to chlorsulfuron in vitro.

A similar synergism is apparent for the TP class of herbicides. Shoot resistance for the single mutants Sur and Sir-13 are 40X and 1X, respectively, and 60X for the double mutant, SB. ALS enzyme data support this synergism observation with 50X and 3X resistance to flumetsulam for the single mutants Sur and Sir-13, respectively, and 200X resistance for the double mutant, SB (FIG. 8). The second mutation observed in SB actually reduces the resistance to chlorsulfuron (a SU class herbicide) observed at the whole-plant level (FIG. 9). For chlorsulfuron, whole plant resistance of the SB double mutant (20X) is reduced by more than 50 fold by the addition of the Sir-13-equivalent mutation ($Ala_{113} \rightarrow Thr$) (1X resistance) to the SU-resistance gene, Sur ($Pro_{188} \rightarrow Ser$) (>1000X resistance) (Table 2). The cause of antagonism between the Sur single mutant and the SB double mutant as yet is unknown. At the ALS enzyme level, a synergistic resistance is also observed with chlorsulfuron (FIG. 10).

It will be appreciated that the selection for imidazolinone resistance can be accomplished first and then the sulfonylurea resistance can be accomplished.

It is intended that the foregoing description be only illustrative of the present invention and that the present invention be limited only by the hereinafter appended claims. Amino acid sequences of FIG. 4 are shown in SEQ ID NOS: 1, 2, 3 and 4.

We claim:

1. A sugar beet plant material consisting of mutated cells with a mutated acetolactate synthase gene encoding the synthase wherein nucleotides are modified from cytosine to thymine at position 562 and guanine to adenine at position 337, wherein the mutated cells have a resistance to both imidazolinone and sulfonylurea herbicides and wherein the resistance is transmitted by conventional cross-breeding of plants produced from the cells and the cells are regenerable to a plant.

2. The material of claim 1 which has been derived from sensitive cells of a parent sugar beet plant, designated as CR1-B deposited as ATCC 97961 and having resistance to sulfonylurea herbicides and no resistance to imidazolinone herbicides, by cultivation of the sensitive cells in a culture medium with the imidazolinone herbicide to select for the mutated cells.

3. The material of claim 1 in a deposit of a seed designated as ATCC 97535 (93R30B).

4. The plant material of any one of claims 1 or 2 as a seed or propagule of the seed.

5. A method of producing a herbicide resistance in a sugar beet plant which comprises:
(a) exposing first cells of the sugar beet to an imidazolinone herbicide with a mutated acetolactate synthase gene encoding the synthase, wherein nucleotides are modified from cytosine to thymine at position 562 and guanine to adenine at position 337 in a culture medium, wherein the first cells have a homozygous trait for resistance sulfonylurea herbicide, in a culture medium; and
(b) selecting for second cells having a resistance to both herbicides, wherein the resistance can be transmitted by cross-breeding of a plant containing the second cells.

6. The method of claim 5 wherein the second cells are derived from the first cells of a sugar beet plant designated as 93R30 (SurSur) deposited as ATCC 97961 by exposing the cells of 93R30 to an imidazolinone herbicide.

7. The method of claim 5 wherein the second cells are in a deposit of a seed designated as ATCC 97535 (93R30B).

8. A method for imparting a herbicide resistance in a sugar beet which comprises:

(a) exposing first cells of sugar beet plant to an imidazolinone herbicide in a culture medium, wherein the first cells have a homozygous resistance sulfonylurea herbicide in a culture medium;

(b) selecting for second cells having a resistance to both herbicides;

(c) growing a first plant from the second cells, wherein the plant has the resistance to the herbicides with a mutated acetolactate synthase gene encoding the synthase, wherein nucleotides are modified from cytosine to thymine at position 562 and guanine to adenine at position 337; and (d) cross-breeding the first plant with a second plant to produce a crossed plant which has the resistance to the herbicides.

9. A method for imparting herbicide resistance to other beets which comprises:

(a) exposing first cells of sugar beet plant to an imidazolinone herbicide in a culture medium, wherein the first cells have a homozygous resistance sulfonylurea herbicide in a culture medium;

(b) selecting for second cells having a resistance to both herbicides;

(c) growing a first plant from the second cells, wherein the plant has the resistance to the herbicides with a mutated acetolactate synthase gene encoding the synthase, wherein nucleotides are modified from cytosine to thymine at position 562 and guanine to adenine at position 337; and (d) cross-breeding the first plant with a second plant to produce a crossed plant which has the resistance to the herbicides.

10. The method of claim 8 wherein the first cells in step (a) are derived from a sugar beet designated as 93R30 deposited as ATCC 97961 by exposing the cells of 93R30 to an imidazolinone herbicide.

11. The method of claim 8 wherein the second cells are in a deposit of a seed designated as ATCC 97535 (93R30B).

12. A method for controlling weeds growing with sugar beet plants which comprises:

(a) planting in a field sugar beet seeds containing cells with a mutated acetolactate synthase gene encoding the synthase wherein nucleotides are modified from cytosine to thymine at position 562 and guanine to adenine at position 337, wherein the mutated cells have a resistance to both imidazolinone and sulfonylurea herbicides and wherein the resistance is transmitted by conventional cross-breeding of plants produced from the cells to produce sugar beet plant; and (b) using an imidazolinone herbicide on the plant in the field to control weeds.

13. The method of claim 12 wherein the plant is derived from sensitive cells of a parent sugar beet plant, designated as CR1-B deposited as ATCC 97961 and having resistance to sulfonylurea herbicides and no resistance to imidazolinone herbicides, by cultivation of the sensitive cells in a culture medium with the imidazolinone herbicide to select for the mutated cells.

14. The method of claim 12 wherein the plant is derived from a seed deposited as ATCC 97535 (93R30B).

* * * * *